United States Patent
Zhu et al.

(10) Patent No.: US 11,795,475 B2
(45) Date of Patent: Oct. 24, 2023

(54) CELL STRAIN FOR REDUCING PRODUCTION OF REPLICATION COMPETENT ADENOVIRUS, AND CONSTRUCTION METHOD AND USE THEREOF

(71) Applicant: CANSINO BIOLOGICS INC., Tianjin (CN)

(72) Inventors: Tao Zhu, Tianjin (CN); Haiyan Cui, Tianjin (CN); Weiwei Chen, Tianjin (CN); Lei Duan, Tianjin (CN); Junqiang Li, Tianjin (CN); Jin Ma, Tianjin (CN); Chunlin Xin, Tianjin (CN); Zhongqi Shao, Tianjin (CN); Xuefeng Yu, Tianjin (CN); Huihua Mao, Tianjin (CN)

(73) Assignee: CANSINO BIOLOGICS INC., Tianjin (CN)

( * ) Notice: Subject to any disclaimer, the term of this patent is extended or adjusted under 35 U.S.C. 154(b) by 792 days.

(21) Appl. No.: 16/806,013

(22) Filed: Mar. 2, 2020

(65) Prior Publication Data

US 2020/0255862 A1 Aug. 13, 2020

Related U.S. Application Data

(63) Continuation of application No. PCT/CN2018/102882, filed on Aug. 29, 2018.

(30) Foreign Application Priority Data

Sep. 1, 2017 (CN) .......................... 201710778032.8

(51) Int. Cl.
*C12N 15/86* (2006.01)
*A61K 39/235* (2006.01)
*C12N 5/071* (2010.01)

(52) U.S. Cl.
CPC ............ *C12N 15/86* (2013.01); *A61K 39/235* (2013.01); *C12N 5/0686* (2013.01)

(58) Field of Classification Search
CPC ..... C12N 5/0686; C12N 15/86; A61K 39/235
See application file for complete search history.

(56) References Cited

FOREIGN PATENT DOCUMENTS

| CN | 107630004 A | 1/2018 |
|---|---|---|
| WO | 2008132729 A2 | 11/2008 |
| WO | 2011086509 A1 | 7/2011 |

OTHER PUBLICATIONS

Imler et al. Novel complementation cell lines derived from human lung carcinoma A549 cells support the growth of E1-deleted adenovirus vectors. Gene Therapy 1996, 3:75-84. (Year: 1996).*
Schiedner et al. Efficient transformation of primary human amniocytes by E1 functions of Ad5: Generation of new cell lines for adenoviral vector production. Human Gene Therapy 2000, 11:2105-2116. (Year: 2000).*
Fallaux et al. New helper cells and matched early region 1-deleted adenovirus vectors prevent generation of replication-competent adenoviruses. Human Gene Therapy 1998, 9:1909-1917. (Year: 1998).*
Rauschhuber et al., Title of the article: Transcriptional activity of inverted terminal repeats of various human adenovirus serotypes, Journal of General Virology, Mar. 1, 2022, vol. 92, pp. 669-674, Place of publication: England.
Imre Kovesdi et al. Title of the article: Adenoviral Producer Cells, Viruses, MDPI, CH, Aug. 16, 2010, vol. 2, pp. 1681-1703, Place of publication: Switzerland.
Stone D, et al. Title of the article: Development And Assessment Of Human Adenovirus Type 11 As A Gene Transfer Vector, Journal of General Virology, Apr. 15, 2005, vol. 79, pp. 5090-5104, Place of publication: England.
Peled M et al, Title of the article: Antiangiogenic systemic gene therapy combined with doxorubicin administration induced caspase 8 and 9-mediated apoptosis in endothelial cells and an anti-metastasis effect, Cancer Gene Therapy Aug. 2008, vol. 15, No. 8, Aug. 2008, pp. 535-542.
European Search Report, Application No. EP 18 85 1666, dated Jun. 9, 2020.
PCT International Search Report, International application No. PCT/CN2018/102882, dated Dec. 12, 2018.
PCT Written Opinion of the International Searching Authority, International application No. PCT/CN2018/102882, dated Dec. 12, 2018.

* cited by examiner

Primary Examiner — Allison M Fox
Assistant Examiner — Jennifer S Spence
(74) Attorney, Agent, or Firm — FLENER IP & BUSINESS LAW; Zareefa B. Flener

(57) ABSTRACT

Provided are a cell strain HEK293.CS for reducing the production of a replication competent adenovirus, and a construction method and the use thereof. HEK293.CS is a safe adenovirus-producing cell line constructed by knocking out a gene fragment homologous to the Ad5 adenovirus E1 gene in HEK293 and providing a template plasmid to replace said gene fragment with a non-homologous sequence that stabilizes the expression of the E1 gene. Compared with the unmodified HEK293 cell strain, HEK293.CS shows no decrease in growth ability and virus production ability, but does not produce a detectable RCA. HEK293.CS can be used for the mass culture of a recombinant human type 5 adenovirus, and reducing the probability of RCA production in the manufacture process of drugs such as vaccines and antibodies.

15 Claims, 3 Drawing Sheets
Specification includes a Sequence Listing.

SEQUENCE LISTING

<160> NUMBER OF SEQ ID NOS: 16

<210> SEQ ID NO 1
<211> LENGTH: 511
<212> TYPE: DNA
<213> ORGANISM: Artificial Sequence
<220> FEATURE:
<223> OTHER INFORMATION: PGK Promoter

<400> SEQUENCE: 1

```
gggggttgggg ttgcgccttt tccaaggcag ccctgggttt gcgcagggac gcggctgctc      60
tgggcgtggt tccgggaaac gcagcggcgc cgaccctggg tctcgcacat tcttcacgtc     120
cgttcgcagc gtcacccgga tcttcgccgc taccttgtg ggcccccgg cgacgcttcc      180 tcgtccgccc ctaagtcggg aaggttcctt gcggttcgcg gcgtgccgga cgtgacaaac     240
ggaagccgca cgtctcacta gtaccctcgc agacggacag cgccagggag caatggcagc     300
gcgccgaccg cgatgggctg tggccaatag cggctgctca gcagggcgcg ccgagagcag     360
cggccgggaa ggggcggtgc gggaggcggg gtgtggggcg gtagtgtggg ccctgttcct     420
gcccgcgcgg tgttccgcat tctgcaagcc tccggagcgc acgtcggcag tcggctccct     480
cgttgaccga atcaccgacc tctctcccca g                                    511
```

<210> SEQ ID NO 2
<211> LENGTH: 460
<212> TYPE: DNA
<213> ORGANISM: Artificial Sequence
<220> FEATURE:
<223> OTHER INFORMATION: ITR+E1A Promoter

<400> SEQUENCE: 2

```
catcatcaat aatatacctt attttggatt gaagccaata tgataatgag ggggtggagt       60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgttttg      180 gtgtgcgccg gtgtacacag gaagtgacaa ttttcgcgcg gttttaggcg gatgttgtag     240
```

```
taaatttggg cgtaaccgag taagatttgg ccattttcgc gggaaaactg aataagagga    300
agtgaaatct gaataatttt gtgttactca tagcgcgtaa tatttgtcta gggccgcggg    360
gactttgacc gtttacgtgg agactcgccc aggtgttttt ctcaggtgtt ttccgcgttc    420
cgggtcaaag ttggcgtttt attattatag tcagctgacg                          460
```

<210> SEQ ID NO 3
<211> LENGTH: 25
<212> TYPE: DNA
<213> ORGANISM: Artificial Sequence
<220> FEATURE:
<223> OTHER INFORMATION: sgRNA1 top strand

<400> SEQUENCE: 3

```
caccgttgtg acgtggcgcg gggcg                                          25
```

<210> SEQ ID NO 4
<211> LENGTH: 25
<212> TYPE: DNA
<213> ORGANISM: Artificial Sequence
<220> FEATURE:
<223> OTHER INFORMATION: sgRNA1 bottom strand

<400> SEQUENCE: 4

```
aaaccgcccc gcgccacgtc acaac                                          25
```

<210> SEQ ID NO 5
<211> LENGTH: 25
<212> TYPE: DNA
<213> ORGANISM: Artificial Sequence
<220> FEATURE:
<223> OTHER INFORMATION: sgRNA2 top strand

<400> SEQUENCE: 5

```
caccgccacc ccctcattat catat                                          25
```

<210> SEQ ID NO 6
<211> LENGTH: 25
<212> TYPE: DNA
<213> ORGANISM: Artificial Sequence
<220> FEATURE:
<223> OTHER INFORMATION: sgRNA2 bottom strand

<400> SEQUENCE: 6

```
aaacatatga taatgagggg gtggc                                          25
```

<210> SEQ ID NO 7
<211> LENGTH: 25
<212> TYPE: DNA
<213> ORGANISM: Artificial Sequence
<220> FEATURE:
<223> OTHER INFORMATION: sgRNA3 top strand

<400> SEQUENCE: 7

```
caccgcctcc gagccgctcc gacac                                          25
```

<210> SEQ ID NO 8
<211> LENGTH: 25
<212> TYPE: DNA
<213> ORGANISM: Artificial Sequence
<220> FEATURE:
<223> OTHER INFORMATION: sgRNA3 bottom strand

<400> SEQUENCE: 8

```
aaacgtgtcg gagcggctcg gaggc                                          25
```

<210> SEQ ID NO 9
<211> LENGTH: 25
<212> TYPE: DNA
<213> ORGANISM: Artificial Sequence
<220> FEATURE:
<223> OTHER INFORMATION: sgRNA4 top strand

<400> SEQUENCE: 9
caccgtactc gctggcactc aagag                                    25

<210> SEQ ID NO 10
<211> LENGTH: 25
<212> TYPE: DNA
<213> ORGANISM: Artificial Sequence
<220> FEATURE:
<223> OTHER INFORMATION: sgRNA4 bottom strand

<400> SEQUENCE: 10
aaacctcttg agtgccagcg agtac                                    25

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tctcgcacat tcttcacgtc                                          20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cgttaaccac acacgcaatc                                          20

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
ctgcttcgcc gagtctaac                                           19

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
ccacatccgt cgcttaca                                            18

<210> SEQ ID NO 15
<211> LENGTH: 18
<212> TYPE: DNA
<213> ORGANISM: Artificial Sequence
<220> FEATURE:

```
<223> OTHER INFORMATION: primer

<400> SEQUENCE: 15
ctgttccaga agccctat                                                 18

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
acacctccgt ggcagata                                                 18
```

CELL STRAIN FOR REDUCING PRODUCTION OF REPLICATION COMPETENT ADENOVIRUS, AND CONSTRUCTION METHOD AND USE THEREOF

CROSS-REFERENCE TO RELATED APPLICATIONS

This application is a continuation of International Application No. PCT/CN2018/102882, filed on Aug. 29, 2018, which claims priority of Chinese patent application No. 201710778032.8 filed on Sep. 1, 2017. The disclosure of the aforementioned application is hereby incorporated by reference in their entirety.

TECHNICAL FIELD

The invention relates to the field of cell strain biotechnology, in particular to a cell strain for reducing production of replication competent adenovirus, and construction method and use thereof.

BACKGROUND

Crispr/Cas9 has been proved to cleave any given DNA by RNA mediation, the cleavage of a target gene by Crispr/Cas9 introduces DNA double-strand breaks (DSBs), and DSBs are repaired by the way of non-homologous end joining (NHEJ) or homologous-directed repair (HDR). NHEJ repair often results in a frame-shift mutation of the target gene at the Cas9 cleavage site, introducing a loss-of-function mutation. The HDR repair way can be used to knock in a gene under the guidance of an exogenous sequence, introducing a gain-of-function mutation. In addition, by using DSBs and providing donors, it is possible to insert or mutate the target sequence in a genome. However, Crispr/Cas9 may cause severe off-target effect in a mammalian cell. To solve the problem of off-target effect, Cas9n nickase (Cas9-D10, a mutated active center) plus two sgRNAs could be used to greatly reduce the off-target effect, but these two sgRNAs should bind to different chains respectively and be close enough, and the PAMs of the two sgRNAs are opposite each other, so that two closely spaced single-strand breaks may form a double-strand break. However, at potential off-target sequences, Cas9n nickase only has a certain probability of causing single-strand breaks, while single-strand breaks are repaired by the base excision repair pathway. In this process, mutations are rarely caused, then the off-target effect is greatly reduced.

The type 5 non-proliferative adenovirus vector currently used removes the region necessary for replication and amplification of an adenovirus, such as the E1/E3 gene, and then loses the ability to propagate in non-permissive cells. Therefore, the E1 gene needs to be inserted in a production cell (such as a HEK293 cell) so as to ensure normal packaging and amplification of the non-proliferating adenoviral vector of the recombinant exogenous gene. However, there is still an E1A Promoter overlapping region of the E1 gene between the Ad5 adenoviral vector and the HEK293 cell, and recombination occurs between the homologous sequences, theoretically there is the possibility of losing a target gene and producing a replication competent adenovirus (RCA).

SUMMARY OF THE INVENTION

The technical problem to be solved by the present invention is to provide a cell strain for reducing the production of a replication competent adenovirus, and solve the risk of producing replication competent adenovirus (RCA) in the process of producing Ad5 recombinant adenovirus by an existing cell strain.

Another technical problem to be solved by the present invention is to provide a method for constructing the above-described cell strain for reducing the production of replication competent adenovirus.

A still another technical problem to be solved by the present invention is to provide use of the above-described cell strain for reducing the production of replication competent adenovirus.

In order to solve the above technical problems, the technical solutions of the present invention are as follows:

A cell strain for reducing the production of replication competent adenovirus, wherein it is a cell strain HEK293, and in the cell strain HEK293 a non-coding region of the cell strain HEK293 E1 gene is replaced with a heterologous control element.

Preferably, the above cell strain for reducing the production of replication competent adenovirus, wherein it is a cell strain HEK293, and in the cell strain HEK293 the ITR and E1A Promoter sequences of the cell strain HEK293 E1 gene is replaced with a heterologous control element.

Preferably, the above cell strain for reducing the production of replication competent adenovirus, wherein it is a cell strain HEK293, and in the cell strain HEK293 the ITR and E1A Promoter sequences of the cell strain HEK293 E1 gene is replaced with a heterologous control element; and wherein the heterologous control element is PGK Promoter, and the base sequence of the PGK promoter is represented by the sequence of SEQ ID NO:1 in the Sequence Listing.

Preferably, the above cell strain for reducing the production of replication competent adenovirus, wherein the ITR and E1A promoter are regions in the genome of the HEK293 cell strain, which are homologous to the gene sequence in the Ad5 adenovirus vector, and which are likely to undergo homologous recombination and thereby lose the target gene.

A method for constructing the above cell strain for reducing the production of replication competent adenovirus, wherein the specific steps are as follows:

(1) designing, synthesizing, and annealing to obtain sgRNA1, sgRNA2, sgRNA3, and sgRNA4;

(2) preparing a PX462.V2.0 plasmid containing Cas9n enzyme, and digesting the plasmid with BsaI;

(3) ligating the four double-stranded sgRNAs obtained in the step (1) respectively to the plasmid recovering from the gel of the enzymatic cleavage in step (2);

(4) preparing a homologous template repair plasmid, adding a left homologous arm PSG4 sequence and a right homologous arm Ad5 sequence to both ends of the PGK Promoter, and ligating the synthesized sequence to PUC57 vector plasmid, and the plasmid map is shown in FIG. 1;

(5) co-transfecting the four plasmids obtained in step (3) together with the homologous repair plasmid in step (4) into HEK293 cells, and a preliminary modified cell strain is obtained by antibiotic screening and monoclonal purification; with identification, if there is no complete replacement in the modified cell strain, the transfection and screening are continued until the ITR and E1A Promoter of E1 gene in the HEK293 cell strain are completely replaced with a PGK Promoter, i.e., a modified cell line is obtained.

Preferably, the above method for constructing the cell strain for reducing the production of replication competent adenovirus, wherein the method for designing and synthesizing sgRNA1, sgRNA2, sgRNA3, and sgRNA4 in the step (1) includes: screening a sgRNA targeting site, designing and synthesizing sgRNA1T, sgRNA1B, sgRNA2T, sgRNA2B, sgRNA3T, sgRNA3B, sgRNA4T, and sgRNA4B; annealing sgRNA1T with sgRNA1B, sgRNA2T with sgRNA2B, sgRNA3T with sgRNA3B, and sgRNA4T with sgRNA4B respectively, so as to form double-stranded sgRNA1, sgRNA2, sgRNA3, and sgRNA4.

Preferably, the above method for constructing the cell strain for reducing the production of replication competent adenovirus, wherein the screening marker used in step (1) is puromycin.

Preferably, the above method for constructing the cell strain for reducing the production of replication competent adenovirus, wherein it is identified by gene sequencing that there is a complete replacement in the cell line modified in step (5), and it is determined by a RCA test that the modified cell line does not produce detectable RCA.

The above cell strain for reducing the production of replication competent adenovirus, wherein it is used for reducing the production of RCA in the manufacture process of a vaccine or antibody.

The above cell strain for reducing the production of replication competent adenovirus, wherein it is used for the mass culture of a recombinant human type 5 adenovirus.

Another aspect of the present invention provides a modified cell or a passage cell thereof for the expression of an exogenous gene, wherein the ITR and E1A Promoter sequence of E1 gene in the cell or its passage cell is replaced with a heterologous control element, and the sequence of the heterologous control element is less than 35% similar to that of the ITR+E1A Promoter.

The E1 protein expressed by E1 gene is an Ad5 adenovirus early replication related protein, which plays a very important role in viral replication. The deletion of E1 gene causes Ad5 adenovirus being unable to replicate, thereby forming a replication defect. E1 consists of two proteins, E1A and E1B, wherein the E1A promoter determines the expression of E1 gene as an E1 protein. ITR (Inverted terminal repeat) is an inverted terminal repeat sequence capable of activating the transcription of E1A. For convenience of description, the present application abbreviates the ITR and E1A Promoter sequences as ITR+E1A Promoter.

In a particular embodiment of the invention, the cell or its passage cell contains 1 copy or more copies of the ITR+E1A Promoter. For example, an HEK293 cell contains 6 copies of ITR+E1A Promoters; a 911 cell contains 1 copy of ITR+E1 A Promoter, and the likes.

In a particular embodiment of the invention, part or all copies of the ITR+E1A Promoters in the cell or its passage cell are replaced with heterologous control elements. For example, among 6 copies of ITR+E1A Promoters in the HEK293 cell, wherein 5, 4, 3, 2 copies, or 1 copy of the ITR+E1A Promoter(s) are/is replaced with heterogeneous control element(s); or 6 copies of the ITR+E1A Promoters are replaced with heterogeneous control elements. Preferably, all copies of the ITR+E1A Promoters are replaced with heterogeneous control elements.

In a particular embodiment of the invention, the heterologous control element is a promoter capable of initiating the expression of E1A in the cell or its passage cell. Preferably, the heterologous control element is a promoter with high affinity for RNA polymerase, directing the expression of a large amount of E1A protein.

In a particular embodiment of the invention, the sequence of the heterologous control element is less than 35% similar to that of the ITR+E1A Promoter, and the lower the similarity to the ITR+E1A Promoter sequence, the more advantageous. For example, the sequence of the heterologous control element is less than or equal to 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, or 0.5%, etc similar to that of the ITR+E1A Promoter sequence.

The similarity described above is obtained by aligning the heterologous control element sequence with the ITR+E1A Promoter sequence through DNAman software.

In a particular embodiment of the invention, the ITR+E1A Promoter sequence is the sequence represented by SEQ ID NO:2 or a homologous sequence thereof.

Illustratively, the homologous sequence has about 60% or more, about 70% or more, 71% or more, 72% or more, 73% or more, 74% or more, 75% or more, 76% or more, 77% or more, 78% or more, 79% or more, 80% or more, 81% or more, 82% or more, 83% or more, 84% or more, 85% Or above, 86% or more, 87% or more, 88% or more, 89% or more, 90% or more, 91% or more, 92% or more, 93% or more, 94% or more, 95% Or above, 96% or more, 97% or more, 98% or more, 99% or more, 99.1% or more, 99.2% or more, 99.3% or more, 99.4% or more, 99.5% or more, 99.6% or more 99.7% or more, 99.8% or more, or 99.9% or more homology to the original sequence.

In a particular embodiment of the invention, the control element is from a group consisting of: a chicken β-actin promoter, a CMV promoter, an HSV TK promoter, and a PGK promoter. The sequence of the PGK promoter is 33% similar to that of the ITR+E1A Promoter; the sequence of the chicken β-actin promoter is 19.44% similar to that of the ITR+E1A Promoter; the sequence of the CMV promoter is 19.31% similar to that of the ITR+E1A Promoter; and the sequence of the HSV TK promoter is 12.64% similar to that of the ITR+E1A Promoter. Preferably, the heterologous control element is a PGK promoter.

In a particular embodiment of the invention, the sequence of the heterologous control element is the sequence represented by SEQ ID NO:1.

In a particular embodiment of the present invention, the modified cell for exogenous gene expression or a passage cell thereof is from a group consisting of: a HEK293 cell, a 911 cell, a pTG6559 cell, and a N52.E6 cell; preferably, the cell is a HEK293 cell. The ITR+E1A Promoter in HEK293 cell is completely replaced with a PGK promoter, which has stable genetic characteristics and can be widely used as an engineering strain for preparing adenovirus.

In a particular embodiment of the present invention, the modified cell for the expression of the exogenous gene or the passage cell thereof is a HEK293 cell, and the HEK293 cell is obtained by completely replacing the ITR+E1A Promoter in the HEK293 cell with a PGK promoter.

In a particular embodiment of the invention, the cell or its passage cell is used for the preparation of an adenovirus carrying or not carrying a gene of interest. Preferably, the cell or its passage cell is used for the preparation of an Ad5 adenovirus carrying or not carrying a gene of interest.

A further aspect of the invention also provides a method for producing an adenovirus, wherein it comprises infecting said cell or a passage cell thereof with an adenovirus. For example, when Ad5 adenovirus is prepared, it is obtained by infecting a HEK293 cell in which the ITR+E1 A Promoter is completely replaced with a heterologous control element (e.g., a PGK promoter) by Ad5 adenovirus.

In a particular embodiment of the present invention, when the Ad5 adenovirus is prepared, the HEK293 cell strain is infected with the Ad5 adenovirus, and the HEK293 cell strain is obtained by completely replacing the ITR+E1A Promoter in the HEK293 cell with a heterologous control element (e.g., a PGK promoter).

The beneficial effects of the invention:

The above-mentioned cell strain HEK293 for reducing the production of replication competent adenovirus is a safe adenovirus-producing cell line constructed by knocking out a gene fragment homologous to the Ad5 adenovirus E1 gene in HEK293 and providing a template plasmid to replace said gene fragment with a non-homologous sequence that stabilizes the expression of the E1 gene. Compared with the unmodified HEK293 cell strain, the modified HEK293 shows no decrease in growth ability and virus production ability, but does not produce a detectable RCA. The specific effects are as follows:

(1) The modification of a HEK293 cell by Crispr/Cas9n technology minimizes off-target effects;

(2) Targeting sgRNA sequences on both ends of ITR and E1A Promoter in the HEK293 cell E1 gene can increase Cas9n cleavage activity and ensure the removal of the original sequence;

(3) The sgRNA, Cas9n and the homologous template repair plasmid are simultaneously transfected into said cell for knocking out the ITR and E1A Promoter sequences of E1 gene in the HEK293 cell, and replacing them with a PGK Promoter;

(4) When sgRNA, Cas9n and the homologous template repair plasmid are simultaneously transfected into said cell, SCR7 is added to inhibit non-homologous repair, improve homologous repair efficiency, and promote the replacement of ITR and E1A Promoter of E1 gene in the HEK293 cell into a PGK Promoter;

(5) The sgRNA, Cas9n and the homologous template repair plasmid are simultaneously transfected into said cell, after screening and identification if there are still the ITR and E1A Promoter sequences of E1 gene, and then go on transfecting again to ensure that a final HEK293 cell does not contain the E1A Promoter sequence;

(6) The modified cell is used for adenovirus culture, and the yield of harvested adenovirus from the modified HEK293 is consistent with that of the HEK293 cell before transformation;

(7) The modified HEK293 and the pre-modified HEK293 are simultaneously subjected to RCA detection so as to confirm that the modified HEK293 cell does not produce any detectable RCA.

DETAILED DESCRIPTION OF EMBODIMENTS

The technical solutions of the present invention will be further described below in conjunction with particular embodiments.

In the following examples, the replacement of the ITR+ E1A Promoter sequence in the HEK293 cell with a PGK promoter is described as an illustrative example. Other heterologous control elements such as a chicken β-actin promoter, a CMV promoter, and a HSV TK promoter have similar results to that of a PGK promoter.

Figure 2:
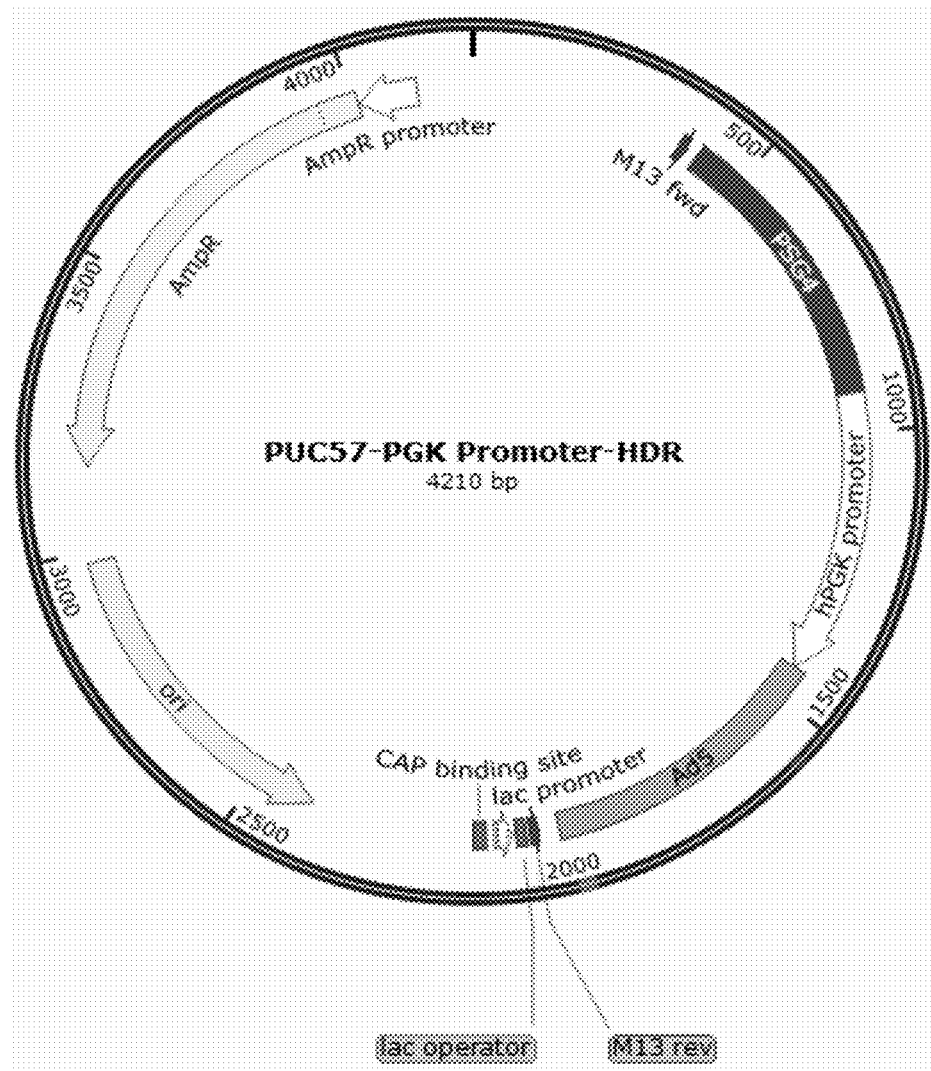
FIG. 2 is a map of the homologous repair template plasmid.

A method for modifying the HEK293 cell by Crispr/Cas9n technology, wherein it comprises a specific target site sequence for ITR and E1A Promoter of E1 gene in the HEK293 cell, the base sequence of the specific target site is represented by SEQ ID NO:2 of the Sequence Listing; the sgRNA oligonucleotide sequence specifically targeting to ITR and E1A Promoter (ITR+E1A Promoter sequence is represented by SEQ ID NO:2 of the Sequence Listing), and the base sequence is shown in Table 1; the designed and synthesized homologous repair template PGK Promoter as shown in FIG. 2, and the base sequence is represented by SEQ ID NO:1 of the Sequence Listing.

TABLE 1 sgRNA sequences

| Names | Sequences |
|---|---|
| sgRNA1 top strand | CACCGTTGTGACGTGGCGCGGGGCG, the sequence represented by SEQ ID NO:3 of the Sequence Listing |
| sgRNA1 bottom strand | AAACCGCCCCGCGCCACGTCACAAC, the sequence represented by SEQ ID NO: 4 of the Sequence Listing |
| sgRNA2 top strand | CACCGCCACCCCCTCATTATCATAT, the sequence represented by SEQ ID NO: 5 of the Sequence Listing |
| sgRNA2 bottom strand | AAACATATGATAATGAGGGGGTGGC, the sequence represented by SEQ ID NO: 6 of the Sequence Listing |
| sgRNA3 top strand | CACCGCCTCCGAGCCGCTCCGACAC, the sequence represented by SEQ ID NO: 7 of the Sequence Listing |
| sgRNA3 bottom strand | AAACGTGTCGGAGCGGCTCGGAGGC, the sequence represented by SEQ ID NO: 8 of the Sequence Listing |
| sgRNA4 top strand | CACCGTACTCGCTGGCACTCAAGAG, the sequence represented by SEQ ID NO: 9 of the Sequence Listing |
| sgRNA4 bottom strand | AAACCTCTTGAGTGCCAGCGAGTAC, the sequence represented by SEQ ID NO: 10 of the Sequence Listing |

The above method for modifying the HEK293 cell by Crispr/Cas9n technology includes the following steps:

S1. Designing and synthesizing a sgRNA specifically targeting to the ITR and E1A Promoter of E1 gene in the HEK293 cell, and annealing to form a double strand;

S2. Constructing a double-stranded sgRNA into a PX462.V2.0 vector; S3. Designing and synthesizing a homologous repair template plasmid; S4. After mixing the sgRNA and the homologous repair template plasmid constructed in steps S2 and S3, they are transfected into the HEK293 cell, then screening a monoclonal cell strain in which E1 gene is successfully replaced, and its RCA forming ability after virus inoculation is detected.

The final concentrations of PX462.V2.0-sgRNA and homologous repair template plasmid in step S4: PX462.V2.0-sgRNA1, PX462.V2.0-sgRNA2, PX462.V2.0-sgRNA3, and PX462.V2.0-sgRNA4 are respectively 20 ng/μL, and the PGK Promoter repair template plasmid is 25 ng/μL.

A method for modifying E1 gene in the HEK293 cell by Crispr/Cas9n system, particularly it includes the following steps:

(1) Selecting the target site of the ITR and E1 Promoter of E1 gene in the HEK293 cell, and designing the specific sequence of sgRNA by using software;

(2) Designing and synthesizing sgRNA and homologous repair template plasmid, and cloning the sgRNA into the BbsI-digested vector backbone to obtain PX462.V2.0-sgRNA;

(3) Mixing the obtained PX462.V2.0-sgRNA with the homologous repair template plasmid to the following final concentrations: PX462.V2.0-sgRNA1, PX462.V2.0-sgRNA2, PX462.V2.0-sgRNA3, and PX462.V2.0-sgRNA4 are respectively 20 ng/µL, and the PGK Promoter repair template plasmid is 25 ng/µL.

(4) Transfecting the mixed PX462.V2.0-sgRNA and the homologous repair template plasmid into the HEK293 cell, and then the cell is subjected to resistance pressurization, thereby screening a gene-editing cell HEK293 in which the sequence of ITR and E1 Promoter of E1 gene is completely replaced.

Example 1

Figure 1:
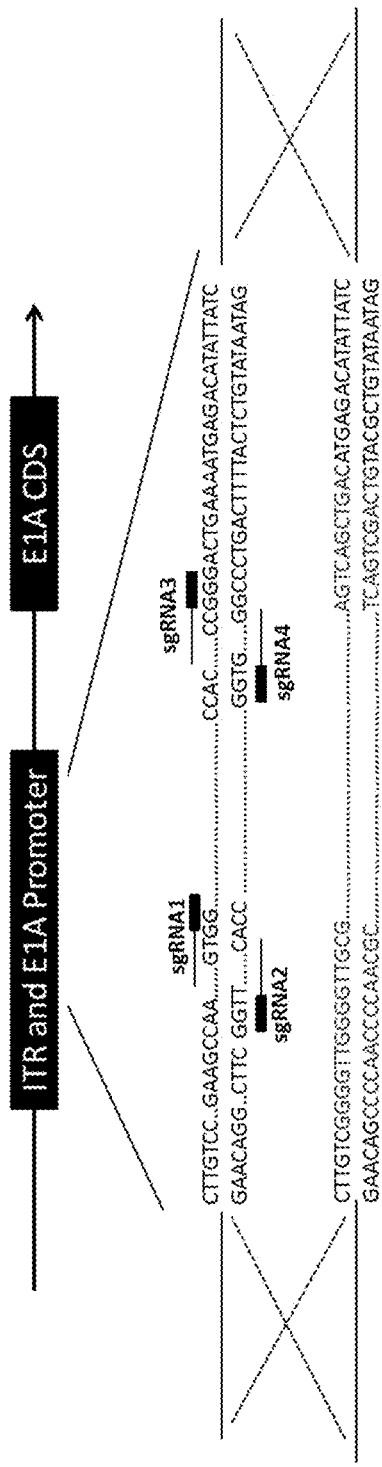
FIG. 1 is a specific target site map of ITR and E1A Promoter of E1 gene in the HEK293 cell modified by Crispr/Cas9n technology.

Constructing a Crispr/Cas9n System for the ITR and E1 Promoter of E1 Gene in the HEK293 Cell First, according to the HEK293 genomic sequence in NCBI, the ITR and E1 Promoter of E1 gene is selected as a target site to design sgRNA. The target site sequence is shown in FIG. 1, and the sgRNA sequence is shown in Table 1 above.

Second, the construction of the specific sgRNA sequence of PX462.V2.0-sgRNA:

(1) Designing and synthesizing the sgRNA that recognizes the ITR and E1 Promoter of E1 gene;

(2) Annealing the synthesized sgRNA oligonucleotide in vitro;

(3) Digesting PX462.V2.0 through the BsaI site and ligating it with sgRNA, then designating as PX462.V2.0-sgRNA.

Finally, a homologous repair template plasmid is designed according to the target site sequence of the sgRNA.

Example 2

Cell Transfection

HEK293 cells are inoculated at a density of $4 \times 10^5$/well in a six-well plate, and transfected when they grow to 70%-90% (about 18-20 h) fusion rate. Transfecting the cells with 20 µL of premixed PX462.V2.0-sgRNA and PGK Promoter template repair plasmid (the following final concentrations: PX462.V2.0-sgRNA1, PX462.V2.0-sgRNA2, PX462.V2.0-sgRNA3, PX462.V2.0-sgRNA4 are respectively 20 ng/µL, and PGK Promoter Repair template plasmid is 25 ng/µL) and 5 µL of Lipo2000 transfection reagent, then adding SCR7 non-homologous recombination inhibitor (final concentration: 0.01 mM) after 12 h, and adding Puromycin (final concentration: 3 µg/mL) after 36 h for screening.

Example 3

Screening Verification

Figure 3:
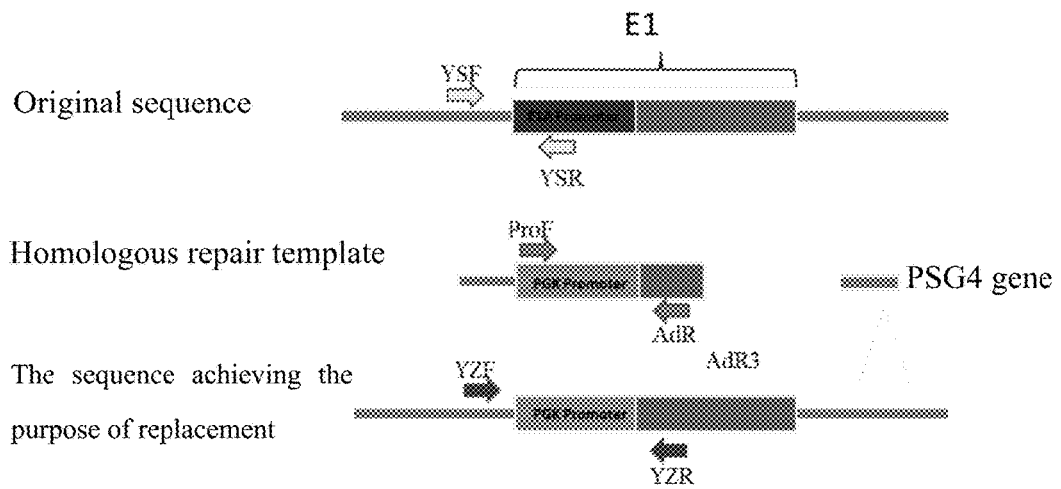
FIG. 3 shows a verification method for verifying the modified cell, determining whether the ITR and E1A Promoter are replaced.

The method shown in FIG. 3 is used to verify whether E1 gene in the modified HEK293 cell is completely replaced, and it includes extracting the genome of the modified cell. If a band can be obtained by amplification through the ProF/AdR primer pair, it is proved that there are original sequences replaced by PGK Promoters. If a fragment can be obtained by amplification through the YSF/R primer pair, it is proved that the original sequence is still present in the replaced cell, and the replacement is not performed completely. Only when a band can be obtained by amplification through the ProF/AdR primer pair, but a band cannot be obtained by amplification through the YSF/R primer pair, it is proved that the ITR and E1A Promoter in the HEK293 cell is completely replaced with a PGK Promoter. If the sequencing result of the fragments amplified by the YZF/R primer pair proves a pure PGK Promoter sequence, it is further proved that the original sequence is completely replaced.

Figure 4:
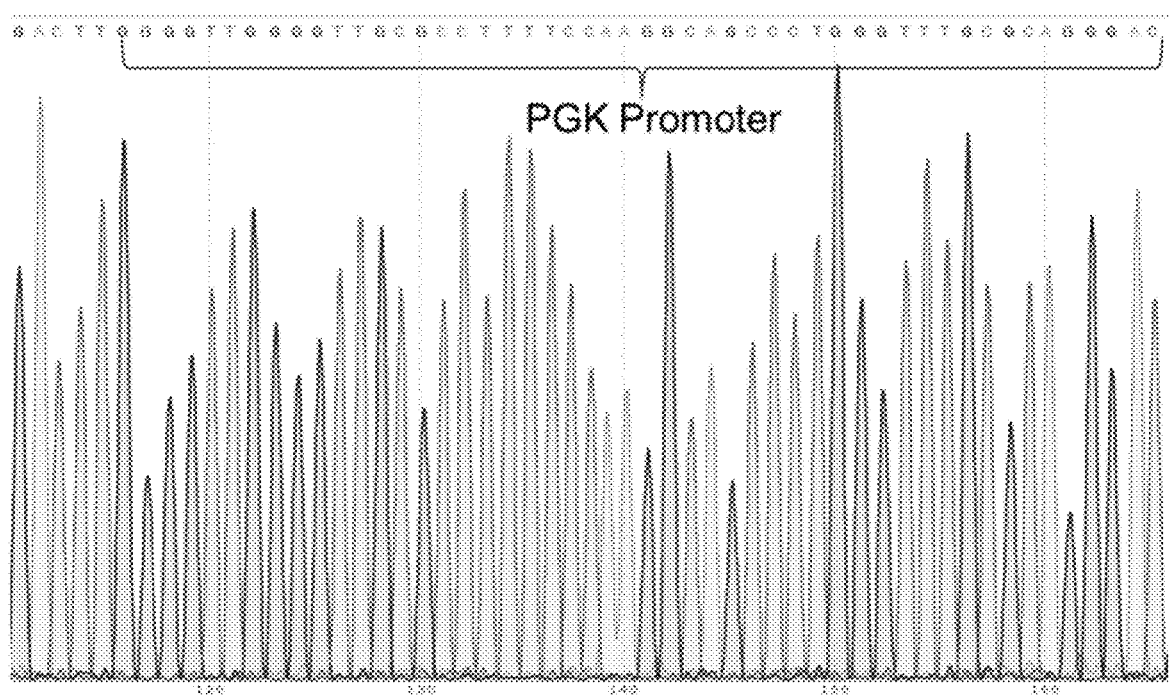
FIG. 4 is a graph showing the sequencing results of E1 gene in the modified HEK293 cell after transformation.

The validation primers are shown in Table 2. It can be seen from the sequencing results in FIG. 4 that the ITR and E1 Promoter in the modified HEK293 cell has been completely replaced with a PGK Promoter.

TABLE 2

Primer sequences for detection

| Names | Sequences |
|---|---|
| ProF | TCTCGCACATTCTTCACGTC, the sequence represented by SEQ ID NO: 11 of the Sequence Listing |
| AdR | CGTTAACCACACACGCAATC, the sequence represented by SEQ ID NO: 12 of the Sequence Listing |
| YSF | CTGCTTCGCCGAGTCTAAC, the sequence represented by SEQ ID NO: 13 of the Sequence Listing |
| YSR | CCACATCCGTCGCTTACA, the sequence represented by SEQ ID NO: 14 of the Sequence Listing |
| YZF | CTGTTCCAGAAGCCCTAT, the sequence represented by SEQ ID NO: 15 of the Sequence Listing |
| YZR | ACACCTCCGTGGCAGATA, the sequence represented by SEQ ID NO: 16 of the Sequence Listing |

Example 4

Detection of the Virus-Producing Ability

HEK293 and the modified HEK293 cells are separately inoculated into 10 cm cell culture dishes, each kind of cells are respectively infected with Ad5-EBOV (GP) and Ad5-TB (Ag85A) viruses having a MOI (multiplicity of infection) of 10. The infected cells are harvested on the third day, at that time most of the cells are lysed and floated, indicating that the viruses are replicated. After harvesting the cells and the supernatant, the viruses are released from the lysed cells after three cycles of repeated freezing/thawing, and the cell debris is removed by centrifugation, followed by purification through column chromatography. The ratio of virus particles/cells is given as a measure of the cell productivity for the growth of different viruses through dividing the total virus particles by the number of cells at the time of infection, thereby determining the virus-producing ability of the cells before and after the transformation. Table 3 shows that the yields of the adenoviral vectors produced by HEK293 or the modified HEK293 cells are nearly equivalent.

TABLE 3

Comparison of virus-producing ability of the HEK293 cell and that of the modified HEK293.CS cell after transformation

| Viruses | Yields of the viruses (IFU/ml) | |
|---|---|---|
| | HEK293 cell | modified HEK293 |
| Ad5-EBOV (GP) | $(3 \pm 0.02) \times 10^9$ | $(2.1 \pm 0.01) \times 10^9$ |
| Ad5-TB (Ag85A) | $(3 \pm 0.03) \times 10^9$ | $(3 \pm 0.02) \times 10^9$ |

Example 5

RCA Detection $3 \times 10^{10}$ or $3 \times 10^{11}$ purified Ad5-GP virus particles after the propagation of HEK293 or the modified HEK293 are used, and RCA is detected by using the existing biological test method (Quality control of clinical grade gene therapy products of recombinant adenovirus. [J]. Zhang Xiaozhi, Lin Hong, Yang Xiaoyan, et al. Chinese Medical Journal, 2004, 84 (10), 849-852.) Zhang Xiaozhi et al., Chinese Journal of Medicine, 2004). The detection results are shown in Table 4. It can be seen from Table 4, when the sample size is $3 \times 10^{10}$ VP, one RCA can be detected in the Ad5-GP viruses propagated in HEK293 cells, and when the sample size is increased to $3 \times 10^{11}$ VP, 13 RCAs are detected in the Ad5-GP viruses propagated in HEK293 cells, but no RCA is detected in the two sample sizes of the Ad5-GP viruses propagated in the modified HEK293 cells.

TABLE 4

Comparison of the RCA formation ability of the HEK293 cell and that of the modified HEK293.CS cell after transformation

| The cell for producing viruses | The number of RCAs in $3 \times 10^{10}$ viruses | The number of RCAs in $3 \times 10^{11}$ viruses |
|---|---|---|
| HEK293 | 1 | 13 |
| The modified HEK293 | 0 | 0 |

The above detailed description of the cell strain for reducing the production of the replication competent adenovirus and construction method and use thereof referring to the Examples are illustrative and not limiting, and several examples can be listed according to the limited scope, therefore the variations and modifications within the spirit of the invention should fall into the protection scope of the invention.

What is claimed is:

1. A cell strain for reducing the production of replication competent adenovirus, wherein the cell strain is HEK293, and the ITR and E1 A Promoter sequences of the cell E1 gene are replaced with a heterologous control element.

2. The cell strain for reducing the production of replication competent adenovirus according to claim 1, wherein the heterologous control element is a PGK Promoter, and the base sequence of the PGK promoter is represented by the sequence of SEQ ID NO:1.

3. A method for manufacturing a vaccine or antibody, wherein a cell strain according to claim 1 is used for the production of non-proliferative adenovirus.

4. The method according to claim 3, wherein the adenovirus is a recombinant human type 5 adenovirus.

5. A modified cell or a passage cell thereof, wherein the ITR and E1A Promoter sequence (abbreviated as ITR+E1A Promoter) of E1 gene in the cell or its passage cell is replaced with a heterologous control element, the sequence of the heterologous control element is less than 35% similar to that of the ITR+E1A Promoter, the cell is a HEK293 cell; and the heterologous control element is selected from a group consisting of: a chicken β-actin promoter, a CMV promoter, an HSV TK promoter, and a PGK promoter.

6. The cell or a passage cell thereof according to claim 5, wherein the cell or its passage cell contains 1 copy or more copies of the ITR+E1A Promoter, and some or all copies of the ITR+E1 A Promoters are replaced with heterologous control elements.

7. The cell or a passage cell thereof according to claim 5, wherein the heterologous control element is less than 35%, 33%, 32%, 31%, 30%, 29%, 28%, 26%, 25%, 23%, 22% or 20% similar to the ITR+E1 A Promoter sequence.

8. The cell or a passage cell thereof according to claim 5, wherein the ITR+E1 A Promoter sequence is the sequence represented by SEQ ID NO:2 or a homologous sequence thereof.

9. The cell or a passage cell thereof according to claim 5, wherein the sequence of the heterologous control element PGK Promoter is the sequence represented by SEQ ID NO:1.

10. A method for producing an adenovirus, wherein the method comprises infecting the cell according to claim 5 or a passage cell thereof with an adenovirus.

11. The method according to claim 10, wherein the adenovirus is Ad5 adenovirus.

12. The cell strain for reducing the production of replication competent adenovirus according to claim 1, wherein the heterologous control element is selected from a group consisting of: a chicken β-actin promoter, a CMV promoter, an HSV TK promoter, and a PGK promoter.

13. The cell strain for reducing the production of replication competent adenovirus according to claim 1, wherein the cell strain contains 1 copy or more copies of the ITR+E1 A Promoter, part or all copies of the ITR+E1A Promoters are replaced with the heterologous control elements.

14. The cell or a passage cell thereof according to claim 5, wherein the cell or its passage cell contains 1 copy or more copies of the ITR+E1A Promoter, all copies of the ITR+E1A Promoters are replaced with heterologous control elements.

15. The cell or a passage cell thereof according to claim 5, wherein the heterologous control element is PGK promoter.

* * * * *